United States Patent
Rees et al.

(10) Patent No.: US 11,728,023 B2
(45) Date of Patent: Aug. 15, 2023

(54) DECISION SUPPORT SYSTEM FOR LUNG VENTILATOR SETTINGS

(71) Applicant: Covidien LP, Mansfield, MA (US)

(72) Inventors: Stephen Edward Rees, Gistrup (DK); Dan Stieper Karbing, Aalborg (DK)

(73) Assignee: Covidien LP, Mansfield, MA (US)

( * ) Notice: Subject to any disclaimer, the term of this patent is extended or adjusted under 35 U.S.C. 154(b) by 495 days.

(21) Appl. No.: 16/841,083

(22) Filed: Apr. 6, 2020

(65) Prior Publication Data

US 2020/0230337 A1 Jul. 23, 2020

Related U.S. Application Data

(63) Continuation of application No. 15/036,553, filed as application No. PCT/DK2014/050387 on Nov. 14, 2014, now abandoned.

(30) Foreign Application Priority Data

Nov. 15, 2013 (DK) ............ PA 2013 70690

(51) Int. Cl.
| | |
|---|---|
| A61B 5/00 | (2006.01) |
| A61B 5/08 | (2006.01) |
| G16H 40/63 | (2018.01) |
| A61M 16/00 | (2006.01) |
| A61M 16/10 | (2006.01) |
| G16H 20/40 | (2018.01) |

(52) U.S. Cl.
CPC ............ *G16H 20/40* (2018.01); *A61B 5/08* (2013.01); *A61B 5/082* (2013.01); *A61B 5/4836* (2013.01); *A61B 5/7275* (2013.01); *A61B 5/7435* (2013.01); *A61M 16/0051* (2013.01); *A61M 16/024* (2017.08); *G16H 40/63* (2018.01); *A61M 2016/003* (2013.01); *A61M 2016/0027* (2013.01); *A61M 2016/103* (2013.01); *A61M 2016/1025* (2013.01); *A61M 2205/502* (2013.01); *A61M 2230/202* (2013.01); *A61M 2230/205* (2013.01); *A61M 2230/208* (2013.01); *A61M 2230/432* (2013.01); *A61M 2230/435* (2013.01)

(58) Field of Classification Search
CPC ........ G16H 20/40; G16H 50/20; G16H 50/30; G16H 50/50; G16H 50/70; G16H 40/63; G16H 40/60; A61M 16/022; A61M 16/024; A61M 16/026; A61M 16/0051; A61B 5/08; A61B 5/082; A61B 5/4836; A61B 5/7275; A61B 5/7271; A61B 5/742; A61B 5/743; A61B 5/7435
See application file for complete search history.

(56) References Cited

U.S. PATENT DOCUMENTS

| | | | |
|---|---|---|---|
| 8,695,593 | B2 | 4/2014 | Tehrani |
| 2002/0169385 | A1 | 11/2002 | Heinonen et al. |

(Continued)

FOREIGN PATENT DOCUMENTS

| | | |
|---|---|---|
| CA | 2839957 A1 | 1/2013 |
| DE | 102012107078 A1 | 2/2013 |
| WO | 2013071404 | 5/2013 |

*Primary Examiner* — Joseph D. Boecker
*Assistant Examiner* — Brian T Khong

(57) ABSTRACT

A ventilator system is capable of displaying complex information patterns in a GUI, thereby allowing a clinician to get subtract complex information from multiple parameters inputs.

25 Claims, 10 Drawing Sheets

(56) References Cited

U.S. PATENT DOCUMENTS

| | | | |
|---|---|---|---|
| 2007/0265611 A1 | 11/2007 | Ignagni et al. | |
| 2008/0295839 A1 | 12/2008 | Habashi | |
| 2009/0094053 A1* | 4/2009 | Jung | G16H 30/20 |
| | | | 705/2 |
| 2010/0217738 A1* | 8/2010 | Sarel | A61B 5/08 |
| | | | 706/47 |
| 2010/0331700 A1* | 12/2010 | Baba | A61B 8/5223 |
| | | | 600/454 |
| 2011/0040713 A1* | 2/2011 | Colman | A61B 5/0836 |
| | | | 703/2 |
| 2011/0249005 A1 | 10/2011 | Hautvast | |
| 2013/0060110 A1 | 3/2013 | Lynn et al. | |
| 2013/0131465 A1* | 5/2013 | Yamamoto | A61B 5/7271 |
| | | | 600/300 |
| 2013/0267793 A1 | 10/2013 | Meador et al. | |
| 2013/0289364 A1 | 10/2013 | Colman et al. | |
| 2013/0296719 A1 | 11/2013 | Packer et al. | |
| 2013/0338459 A1* | 12/2013 | Lynn | A61B 5/14551 |
| | | | 600/323 |
| 2013/0345572 A1 | 12/2013 | Karbing et al. | |
| 2014/0275819 A1 | 9/2014 | Kassem et al. | |
| 2016/0121064 A1 | 5/2016 | Rees et al. | |

* cited by examiner

DECISION SUPPORT SYSTEM FOR LUNG VENTILATOR SETTINGS

CROSS-REFERENCE TO RELATED APPLICATION

This application is a continuation of U.S. application Ser. No. 15/036,553, filed May 13, 2016, which is the U.S. national stage of PCT/DK2014/050387 filed Nov. 14, 2014, which claims priority of patent application DK PA 2013 70690 filed Nov. 15, 2013. The entire content of each application is incorporated herein by reference.

FIELD OF THE INVENTION

The present invention relates to a decision support system for lung ventilator settings. In particular, the present invention relates to a decision support system for lung ventilator settings, which displays technical features of measured physiological parameters providing the clinician with decision support in relation to ventilator settings.

BACKGROUND OF THE INVENTION

Patients residing at the intensive care unit typically receive mechanical support for their ventilation. Selecting the appropriate level of mechanical ventilation is not trivial, and it has been shown that appropriate settings can reduce mortality [1].

A challenge with the settings of a mechanical ventilator is that each setting may be beneficial for one physiological parameter of the patient but negative for another physiological parameter. Currently the clinician may get help by ventilator screens, extra devices monitoring physiological parameters (capnograph, pulseoximeter, monitor, etc.) and alarm settings if something is wrong.

Clinicians may get stressed by the vast number of settings, physiological parameters, screens, and the relationship between these values and their impact on therapeutic decisions in relation to conflicting goals. Stress and lack of overview can lead to errors, which can be fatal in an ICU [2, 3].

Hence, an improved system for minimizing failure in ventilator settings would be advantageous, and in particular a more efficient and/or reliable system which can minimize stress of the clinician during ventilator setup would be advantageous.

SUMMARY OF THE INVENTION

The present invention relates to a decision support system, which enables the clinician to get an overview of physiological parameters of a patient in relation to current and future ventilator settings by presenting scoring values calculated/determined from physiological parameters, respirator settings and clinical preferences. The scoring values are displayed for different pairs of scoring values of the patients, which have conflicting effects in response to over-ventilation and under-ventilation in a graphical user interface (GUI). An example is lung trauma vs. acidosis, where acidosis may be compensated for by increasing ventilation pressure. On the other hand increased ventilation pressure may result in lung trauma. To complicate the case further, the different physiological parameters have different scales and units, and a change in the different physiological parameters (e.g. in response to changed ventilator settings) therefore reach critical levels on different scales. Overall, these differences make it difficult for the clinician to maintain an overview for all parameters, their relation to clinical preferences and the balancing of these against each other simply by looking at measured numbers for each parameter. To overcome this problem the inventors have established different preference functions (CPF) (see FIG. 6) for each parameter which translates relevant physiological parameters and ventilator settings into a unified scale (scoring values). These scoring values simplify the decision phase for the clinician by having a unified value for when and how action should be taken. These functions may be adjusted according to specific patient information or other requirements. For example, the translation from physiological variables and settings to preferences may be further improved by implementing physiological models, which would further allow prediction of patient response to changes in settings and the relation of this response to clinical preferences.

Current aids for setting mechanical ventilation are limited. Measured physiological variables are displayed on different devices and are displayed individually with the help to clinicians being constituted by alarms on individual values. As such, clinicians are assisted in finding the variable of priority at present, but not how this is related to overall physiology or clinical preferences. Experiments have been made with configural displays, that is, displays where a graphical figure such as a face or a physiological analogy to the respiratory system is displayed instead of individual numbers. Whilst these may allow clinicians an easier detection of when and how the patient's status is poor, these attempts have not considered how clinical preferences are related to the physiology and current options for setting the ventilator. Preference functions, which can convert measured or predicted physiological variables and ventilator settings into scoring variables allowing a common scaling across different variables have been presented in relation to minimizing risk of barotrauma, acidosis/alkalosis, Oxygen toxicity and absorption atelectasis and hypoxia [5]. However, the scoring variables were presented directly as a table preventing easy and safe interpretation by clinicians.

Thus, an object of the present invention relates to the provision of a mechanical ventilation system which solves the above problem of the prior art in relation to displaying patient status information in a manner assisting the clinician in setting/adjusting ventilator settings.

Another object is the provision of integration of physiological variables in a single device and calculation of preference zones, which gives easy and safe interpretation of the relation between several physiological variables and clinical preferences in one graphical display. A further object is separation of scoring values into two groups allowing easy detection of the risk of over- and under-ventilating the patient, which is important in minimising the time on the ventilator and mortality of the patient. Thus, one aspect of the invention relates to a mechanical ventilation system for respiration aid of an associated patient, the system being adapted for providing decision support for choosing a ventilation strategy of said (associated) patient, the system comprising:
  ventilator means capable of mechanical ventilating said (associated) patient with air and/or one or more medical gases;
  control means, the ventilator means being controllable by said control means by operational connection thereto;
  first measurement means arranged for measuring parameters of the inspired gas, the first means being capable of delivering first data to said control means;

optionally, second measurement means arranged for measuring the respiratory feedback of said (associated) patient in expired gas, the second means being capable of delivering second data to said control means;

third measurement means arranged for measuring one or more blood values of said (associated) patient, the third means being capable of delivering third data to said control means, the control means applying a set of preference functions (CPF) to convert the first data, the third data, and optionally the second data, of the (associated) patient into corresponding scoring values;

the system comprising a graphical user interface (GUI) with a multi-dimensional coordinate system, wherein at least one pair of scoring values is arranged for being displayed in the coordinate system, wherein each pair of scoring values comprises a first scoring value being a translated variable related to over-ventilation of the (associated) patient, the first scoring value being displayed at an axis indicative of over-ventilation in a first direction in the GUI, the first scoring value being displayed at a distance from a first starting point corresponding to the first scoring value, and a second scoring value being a translated variable related to under-ventilation of the (associated) patient, the second scoring value being displayed at an axis being indicative of under-ventilation in a second direction in the GUI, the second scoring value being displayed at a distance from a second starting point corresponding to the second scoring value.

In the present field a device or system capable of performing mechanical ventilation may also be named an artificial breathing machine, a life support device, or, more popularly, a respirator.

Decision Support:

In the present context the term "decision support" should be understood in the broadest sense of the term, decision support covers any means for assisting the user, here the clinician, in making the decision. This includes organization, integration and presentation of data as well as providing suggestions for rational decisions.

Preference Function:

The term "preference function" covers any means for translating a set of preferences, here clinical, into mathematical form, e.g. as a function such as an exponential curve, logical rule set etc. Preference functions are also known as utility theory, and can be presented in the form of utility or penalty associated with a variable. As used in here preference functions translates input in the form of ventilator settings and physiological variables into scoring values annotated e.g. S1, S2, . . . , S6, . . . , Sn. Thus, the term "translate" may, in the context of the present application, be understood to mean transforming, (re)calculating, normalizing, etc., as it will readily be appreciated by a skilled person in this field.

Preference Zone:

In the present context, the term preference zone relates to the calculated graphical display of one or more scoring values calculated using preference functions. Preference zones are preferably illustrated together for several clinical preferences in one combined illustration, where the graphical display may confer information as to the relation between different scoring variables, and the combined display may confer information concerning the combined quality of ventilator therapy and status of the patient.

Over-Ventilation

In the present context the term "over-ventilation" relates to excessive ventilator support. Excessive ventilation may result in mechanical lung trauma, alkalosis, ventilator dependency, oxygen toxicity, haemodynamic adverse effects, etc.

Under-Ventilation

In the present context the term "under-ventilation" relates to insufficient ventilator support. Insufficient ventilation may result in acidosis, stress, low oxygenation, etc.

It may be advantageous to display the scoring values from a common starting point in the multi-dimensional coordinate system. Thus, in an embodiment each pair of plotted scoring values has a common starting point (e.g. origin 'O') in the multi-dimensional coordinate system. FIG. 2A shows a specific example of how scoring values can be displayed from a common starting point.

It may also provide better overview for the clinician if scoring values indicative of low risk is presented closest to the starting point. As mentioned above the starting point may be a common starting point for all pairs. Thus, in an embodiment scoring values displayed closer to the starting point is indicative of lower patient risk than values plotted at greater distance from the starting point. In this context it is to be understood that the patient risk relates to the specific physiological parameter in question unless otherwise stated. To improve the displayed overview further, the values for each pair may be displayed in opposite directions. Thus, in an embodiment the scoring values of a pair are displayed in opposite directions. In FIG. 2A the pair S1 and S4 will be displayed in opposite directions. Similarly, in FIG. 9 each pair is displayed in opposite directions.

Similar, the shape of the multi-dimensional coordinate system may also improve the overview. Thus, in an embodiment the multi-dimensional coordinate system has an outer shape being a polygon, each corner in the polygon and the center (O) of the polygon representing an axis of the scoring values, e.g. S1, . . . , S6, along which the scoring values are plotted. FIGS. 2, 4 and 9 provides example of shapes, which may be used according to the invention depending on the number of pairs. Preferably, each pair comprises two scoring values. Thus, in yet an embodiment the polygon has an equal number of corners, such as 2-20 corners, such as 2-10 corners such as 2-8 corners, such as 4-6 corners, or such as 6 corners.

The multi-dimensional coordinate system could also have other shapes than a polygon, with the maximum value of the scoring value being positioned at the circumference of the coordinate system. Thus, in a further embodiment the multi-dimensional coordinate system is a circle or circular shape (such as an oval), and wherein the circumference of the circle or circular shape and the center of the circle (or circular shape) representing an axis of the scoring parameters S1, . . . , S6 along which the scoring parameter are plotted/displayed. Examples of such round shapes are also presented in FIG. 4.

It may be advantageous that the coordinate system comprises two zones, one indicative of scoring parameters representative for over-ventilation and one zone representative for under-ventilation. Thus, in a further embodiment the coordinate system is divided by a line through the center, dividing the coordinate system into two half's, one half indicative of over-ventilation of the patient and the second half indicative of under-ventilation of the patient. It is to be understood that such line does not need to be displayed in the GUI. The skilled person would for example be able to understand that an upper half relates to over-ventilation and the lower half relates to under-ventilation without the line being displayed. FIG. 2A shows such an example where the dotted line divides the coordinate system into two such half's.

The GUI may also display the different pairs of scoring values from different starting points for each pair. Thus, in an embodiment the starting point for each pair begins at different points at a line in the multi-dimensional coordinate system dividing the coordinate system into two half's, one half indicative of over-ventilation of the patient and the second half indicative of under-ventilation of the patient. FIG. 9 shows examples of such display formats.

The area formed by connecting each plotted/displayed scoring value form a polygon or other shape around the center (also referred to in here as "preference zone) may be indicative of an overall scoring value for the specific patient with the specific ventilator setting. Thus, in an embodiment the neighbouring displayed scoring values are connected with lines forming an area (or preference zone) in the GUI. In yet an embodiment the GUI presents a value and/or indicator for the area formed. FIG. 2C shows an example of such area in a coordinate system. In FIG. 9, examples are displayed where the overall area is the sum of individual areas determined for each pair of scoring values. Thus, calculation of the total area provides a total scoring of the current status of the patient and the appropriateness of the mechanical ventilator settings. The same may be the case for an advice or a simulated situation. The system may be adapted for keeping each scoring value within certain limits.

In one embodiment the converted scoring values represents patient risk values wherein all patient risk values have been normalized to have comparable patient risk values.
History It may also be advantageous if the system was capable of displaying scoring values going back in time thereby providing a historic picture of the calculated scoring values for the patients displayed in an easy conceivable format. Thus, in an embodiment the system is arranged for presenting an overview over scoring values and/or areas determined at earlier time points. Such historic values may be displayed simultaneously with current values or as a different setting in the GUI.

By comparing the areas over time information relating to the ventilator setting may be determined. Thus, in yet a further embodiment decreasing areas 15 over time, is indicative of improved ventilation parameters and wherein increasing areas over time is indicative of suboptimal ventilation parameters.
Modelled/Simulated By using preference functions, it may be possible to model/simulate how the patient may respond to changes in ventilator settings. Thus, in yet an embodiment the system is arranged to output scoring values and/or areas in the GUI based on suggested input ventilation parameters by a user.

In yet an embodiment the system using a physiological model (MOD) arranged for generating outcome variables, which, via preference functions, are transformed into modelled/simulated scoring values and modelled/simulated areas. Examples of physiological models and parameters included in such models, which may be implemented according to the present invention are presented in in FIGS. 5-7 and the corresponding text in the detailed description section.
Advice It may also be advantageous if the system was able to give decision support in the form of new ventilator settings which would be advisable based on inputted information on the patients physiological parameters (or scoring values). Again, the system could be arranged for implementing the described physiological models (MOD). Thus, in yet an embodiment the system is arranged to output an advice for a ventilation strategy of the patient and display modelled scoring values a polygon zones based on said advice, the system using a physiological model (MOD) to generate said advice. The system may base its advice on a model, which minimizes the area of the polygon zones, without any of the scoring values exceeds predetermined threshold levels. Thus, the system may try to minimize the scoring values and thus, also minimize the area/preference zone in the coordinate system. In yet an embodiment, the control means are adapted for using the first data, optionally, the second data and the third data in a physiological model (MOD) of the patient with physiological variables.

As described above the system is arranged for displaying/plotting one or more pairs of scoring values in the GUI. In an embodiment, the pairs of scoring values are selected from the group consisting of:
- mechanical lung trauma vs. acidosis; and/or
- oxygen toxicity vs. low oxygenation; and/or
- stress vs. ventilator dependency; and/or
- Volutrauma vs. atelectrauma and/or
- Alveolar derecruitment vs. haemodynamic adverse effects of high ventilator pressure.

Mechanical Lung Trauma:

"Mechanical lung trauma" is to be understood as mechanical damage or mechanical stress to patient organs and the following physiological effects thereof. In the clinic, there is of course a preference for avoiding risk of mechanical lung trauma. Damage may be induced in several ways; e.g. damage due to high volumes and/or pressures during each breath (often termed volutrauma), damage due to high peak pressures causing rupture of alveolar and capillary membranes (often termed barotrauma), damage due to repetitive opening and closing of alveoli (often termed atelectrauma), damage due to spill over of inflammatory agents (often termed biotrauma), damage of high frequencies such as dynamic hyperinflation due to trapping of gas during expiration and inappropriateness of high frequencies per se (no general term). Clinically measurable variables and ventilator settings for indicating risk of mechanical lung trauma include: Inspiratory and expiratory pressure at the different phases of inspiration and expiration such as plateau pressure at end inspiration, set volumes and pressures on the ventilator such as tidal volume, inflammatory markers, pressure difference across the alveolar membrane as for example can be measured using a pressure transducer in an esophageal catheter combined with pressure measurements at the mouth.

Management of mechanical ventilation requires the clinician to consider several conflicting clinical preferences: pressures or volume settings, for example, should be set so that lung regions are kept open and collapsed regions are opened (recruited) and gas exchange between capillary blood and alveolar gas is secured. However, these settings should not be at too high levels where there is increased risk of causing mechanical injury to the patient's respiratory system, an effect often called ventilator-induced lung injury. This is a complex problem, which requires the clinician not only to consider the ventilator settings per se, but also other physiological parameters displayed on other devices than the mechanical ventilator. These should be integrated to a physiological and pathophysiological picture of the patient and related to the different clinical preferences, and thereafter the clinician tries to predict how the patient will respond to changes in ventilator settings and how this response will be related to patient physiology and clinical preferences.

Acidosis/Alkalosis

In the clinic, there is a preference for avoiding acidosis and alkalosis and the negative associated effects. Clinically measurable variables for indicating acidosis and alkalosis include: values of pH, concentration of hydrogen ions, concentration of carbon dioxide, concentration of anions, concentration of cations etc. measured in blood (e.g. arterial, peripheral venous, central venous, mixed venous), calculated values indicative of acid base status such as base excess, strong ion difference etc, non-invasive means for indicating acid-base status such as end-tidal concentration of carbon dioxide and non-invasive measurement of tissue and blood carbon dioxide values.

Ventilator Dependency:

In the clinic, there is a preference for minimizing the risk of effects of prolonged time on mechanical ventilation. These effects include respiratory muscle atrophy and weakness, work of breathing, ventilator associated pneumonia, changes in respiratory drive and immobilisation effects. Clinically measurable variables for indicating risk of ventilator dependency include: respiratory frequency, minute ventilation, work of breathing, oxygen consumption, carbon dioxide production, ventilatory pressures, volumes and flows, pattern of ventilation etc.

Stress:

In the clinic, there is a preference for avoiding stress to the patient's respiratory muscles, metabolism, cardiac system and mental state inappropriately, which can result in worsening patient status. Clinically measurable variables for indicating risk of stressing the patient include: The rapid shallow breathing index (respiratory frequency divided by tidal volume), respiratory frequency, minute ventilation, work of breathing, oxygen consumption, carbon dioxide production, ventilatory pressures, volumes and flows, pattern of ventilation, Borg scale and other indications provided by the patient in response to questions or detected by the clinician through visual inspection or palpation, etc.

Oxygen Toxicity:

There is a clinical preference for avoiding the negative effects of high levels of oxygen in the inspiratory gas, these effects including toxic effects, i.e. cell death due to high levels of oxygen in tissues, absorption atelectasis, i.e. collapse of regions with low ventilation to perfusion ratio, and increased dependency on mechanical ventilation. Clinically measurable variables for indicating risk of oxygen toxicity include: level of oxygen in inspired gas and oxygen level in the tissue.

Low Oxygenation:

There is also a clinical preference for avoiding the risk of low levels of oxygen in blood and tissues of the body. Clinically measurable variables for indicating risk of low oxygenation include: level of oxygen in inspired gas, tissue levels of oxygen, saturation, partial pressure and concentration of oxygen in blood (arterial, peripheral venous, capillary, central and mixed venous), pulse oximetry oxygen saturation, oxygen delivery, tissue oxygen levels etc.

Haemodynamic Adverse Effects:

There is a clinical preference for avoiding the risk of haemodynamic adverse effects of high ventilator pressures and volumes. These effects include reduced cardiac output and hence delivery of oxygen to the tissues, shock, cardiac failure etc. Clinically measurable variables for indicating risk of haemodynamic adverse effects include: ventilator pressures and volumes such as positive end-expiratory pressure, levels of pressure in blood (arterial, pulmonary arterial, central venous, and peripheral venous) and calculated variables based on these pressure levels such as mean arterial pressure (MAP), venous return, cardiac output, systemic vascular resistance, heart rate, pulse etc.

Alveolar Derecruitment:

There is clinical preference for avoiding the effects associated with derecruitment of alveoli, i.e. the small air sacs where gas exchange occurs in the lungs. Alveolar derecruitment is a common term for collapse of alveoli, which result in worsening of gas exchange and increase risk of mechanical trauma to the lung tissue to develop. Prevention of alveolar derecruitment normally encompasses use of recruitment manoeuvres to open collapsed alveoli by applying high pressures for short periods of time and use of positive-end expiratory pressure. Clinically measurable variables for indicating risk of alveolar derecruitment include: ventilator pressures and volumes such as positive end-expiratory pressure, respiratory system compliance, shape of the pressure-volume relationship of the respiratory system, functional residual capacity (FRC), levels of extra-vascular lung water etc.

In a preferred embodiment, the pairs of scoring values are selected from the group consisting of:
mechanical lung trauma vs. acidosis;
oxygen toxicity vs. low oxygenation; and/or
stress vs. ventilator dependency.

The system may also be arranged for taking into account information relating to the specific patient. Thus, in an embodiment, the decision support system is arranged for receiving one or more therapeutic input parameters relating to the patient, wherein the system is arranged to recalibrate the preference functions (CPF) based on said therapeutic input parameters, thereby also recalibrate the scoring values generated by the system. The system may also be adapted for changing the weighing of each preference function based on the therapeutic input parameters. The advantage of using therapeutic input parameters is that the system can be adjusted to the specific patient thereby fine-tuning the displayed data and improving the decision support. Examples of specific therapeutic input parameters are information on head trauma (influence acid/base preferences), age, sex, clinical history, medication, and/or patient group.

In another aspect, the present invention relates to a computer system for cooperating with, and optionally controlling, an (associated) mechanical ventilation system for respiration aid of an associated patient, the computer system being adapted for providing decision support for choosing a ventilation strategy of said (associated) patient, the associated mechanical ventilation system comprising:
ventilator means capable of mechanical ventilating said (associated) patient with air and/or one or more medical gases;
first control means, the ventilator means being connectable to said first control means by operational connection thereto;
first measurement means arranged for measuring parameters of the inspired gas, the first means being capable of delivering first data to said first control means;
optionally, second measurement means arranged for measuring the respiratory feedback of said (associated) patient in expired gas, the second means being capable of delivering second data to said first control means;
third measurement means, arranged for measuring one or more blood values of said patient, the third means being capable of delivering third data to said first control means, the computer system comprising:

second control means applying a set of preference functions to convert the first data, the third data, and optionally the second data, of the patient into corresponding scoring values; and a graphical user interface (GUI) with a multi-dimensional coordinate system, wherein at least one pair of scoring values is arranged for being displayed in the coordinate system, wherein each pair of scoring values comprises a first scoring value being a physiological variable related to over-ventilation of the patient, the first scoring value being displayed at an axis indicative of over-ventilation in a first direction in the GUI, the first scoring value being displayed at a distance from a first starting point corresponding to the first scoring value, and a second scoring value being a physiological variable related to under-ventilation of the patient, the second scoring value being displayed at an axis being indicative of under-ventilation in a second direction in the GUI, the second scoring value being displayed at a distance from a second starting point corresponding to the second scoring value.

It is worth mentioning that the invention is particularly advantageous in that the computer system may be implemented independently from a mechanical ventilation system by receiving data obtained from such a mechanical ventilation system. Thus, by the term "associated" above, it is emphasized that the mechanical ventilation system does not form part of the computer system. Thus, the first control means of the mechanical ventilation system and the second control means of the computer system may be separate entities, or they may form a single entity. The data may be received directly and/or continuously, or the data can be received from a storage entity at discrete times, regularly or upon choice of a user. Thus, the computer system according to the invention may be applied both for continuous surveillance and decision support of a patient and/or for analysis of earlier data, e.g. obtained from a patient file with the appropriate data therefore.

Colouring of Lines/Areas

The information in the GUI may be further expanded by also using colour codes or colour scaling. Thus, in an embodiment the colouring of lines and/or areas are indicative of the total patient risk. For example if an area is e.g. green the total penalty is low, if an area is yellow the penalty is medium and if the colour is red the total penalty is high.

In another embodiment, the colouring of lines and/or areas are indicative of extra patient risk in addition to risks presented on the axes. For example, if the whole area is coloured red a risk of "adverse haemodynamic effects" is detected.

In another aspect, the invention relates to a computer program product being adapted to enable a computer system comprising at least one computer having data storage means in connection therewith to control mechanical ventilation system for respiration aid of an associated patient according to the invention.

This aspect of the invention is particularly, but not exclusively, advantageous in that the present invention may be accomplished by a computer program product enabling a computer system to carry out the operations of the mechanical ventilation system for respiration aid of an associated patient of the invention when down- or uploaded into the computer system. Such a computer program product may be provided on any kind of computer readable medium, or through a network. Thus, it is contemplated that the invention may be implemented by uploaded and executing a computer program product on a computer system adapted for cooperating with, and optionally controlling, an already existing mechanical ventilation system.

The individual aspects of the present invention may each be combined with any of the other aspects. These and other aspects of the invention will be apparent from the following description with reference to the described embodiments.

BRIEF DESCRIPTION OF THE DRAWINGS

The method according to the invention will now be described in more detail with regard to the accompanying figures. The figures show one way of implementing the present invention and is not to be construed as being limiting to other possible embodiments falling within the scope of the attached claim set.

The present invention will now be described in more detail in the following.

DETAILED DESCRIPTION OF THE INVENTION

As described above, the core aspect of the invention is the use of preference functions to calculate scoring values and corresponding preference zones/areas 15 from clinically measured variables allowing integration of relevant mechanical ventilation variables for a patient into a single presentation covering the contrasting preferences related to mechanical ventilation helping the clinician to minimise risk of over-ventilating and under-ventilating the patient.

Figure 1:
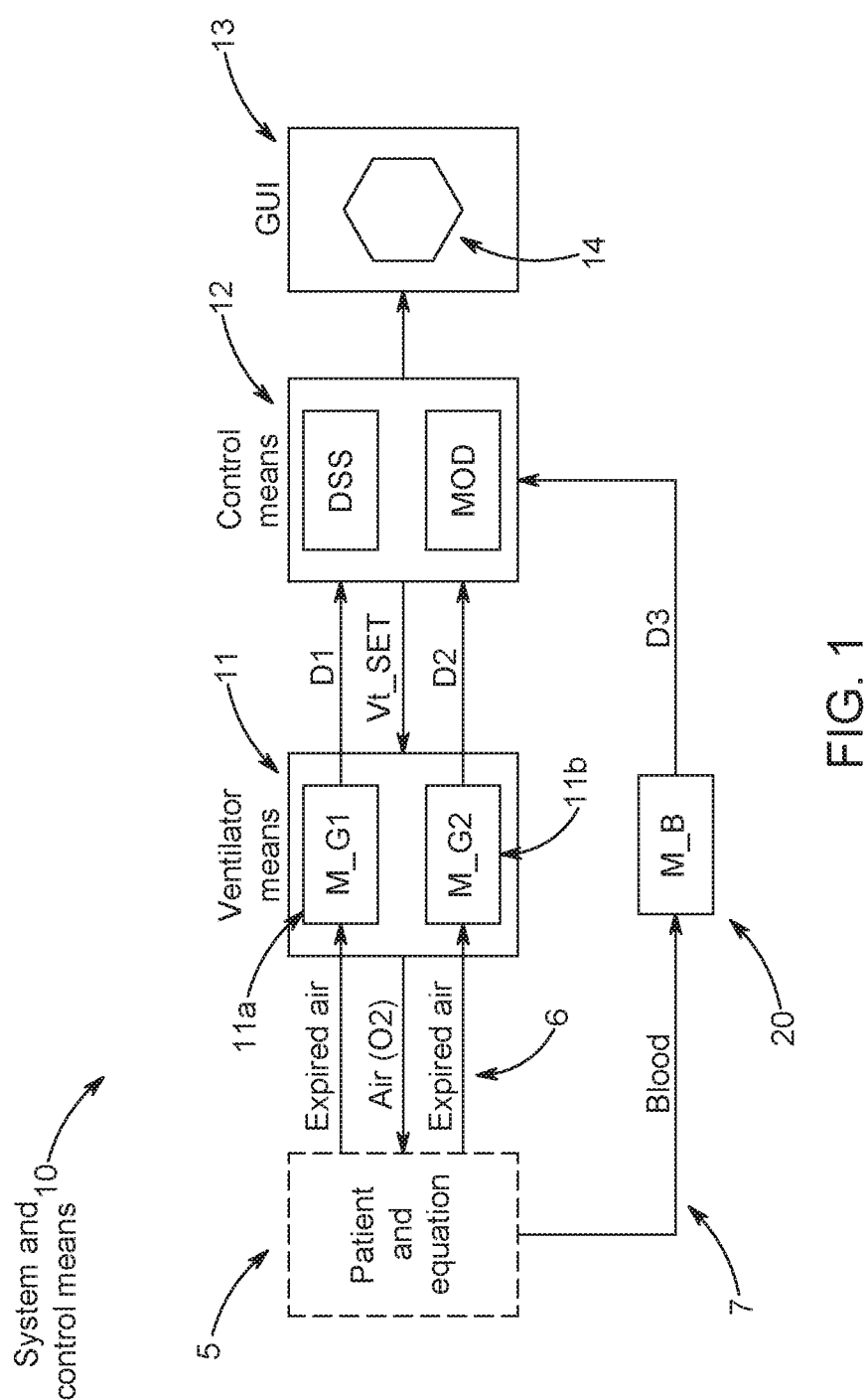
FIG. 1 is a schematic drawing of a mechanical ventilation system according to the present invention.

FIG. 1 is a schematic drawing of a mechanical ventilation system 10 for respiration aid of an associated patient 5, P, the system being adapted for displaying/plotting information of physiological parameters in a manner providing the clinician with information which is difficult to subtract from mere number values. The respiration aid may be fully controlled or supported.

The system comprises ventilator means 11, VENT capable of mechanical ventilating said patient with air and/or one or more medical gases, e.g. oxygen and/or nitrogen. Conventional ventilator systems currently available may be modified or adapted for working in the context of the present invention.

Furthermore, control means 12, CON is comprised in the system 10, the ventilator means 11 being controllable by said control means 12 by operational connection thereto, e.g. appropriate wirings and interfaces as it will be appreciated by the skilled person working with mechanical ventilation.

Additionally, measurement means 11*b*, M_G2 are arranged for measuring the respiratory feedback of said patient in the expired gas 6*b* in response to the mechanical ventilation, e.g. respiratory frequency or fraction of expired carbon dioxide commonly abbreviated $FECO_2$, cf. the list of some well-known abbreviations below. The measurement means are shown as forming part of the ventilator means 11, but could alternatively form an independent entity with respect to the ventilator means without significantly change the basic principle of the present invention. Similarly, the computer system according to the invention may work independently from a mechanical ventilator.

Additionally, measurement means 11*b*, M_G2 are arranged for measuring parameters of the inspired gas 6*a*, the first means being capable of delivering first data D1 to said control means. It should be noted that the first data D1 may also include the ventilator settings (Vt_SET).

The measurement means M_G (1 and 2) are capable of delivering the first data D1 and the second data D2 to the control means 12 CON by appropriate connection, by wire, wirelessly or by other suitably data connection.

The control means 12 CON is also capable of operating the ventilation means by providing ventilatory assistance so that said patient 5 P is at least partly breathing spontaneously, and, when providing such ventilatory assistance, the control means being capable of changing one, or more, volume and/or pressure parameters Vt_SET of the ventilator means so as to detect changes in the respiratory feedback in general of the patient by the measurement means M_G (1 and 2).

The control means is further being arranged for receiving third data D3, preferably obtainable from blood analysis of said patient performed by blood measurement means M_B 20, the third data being indicative of the respiratory feedback in the blood of said patient, e.g. pHa, PACO2, PAO2 etc. Notice that the blood measurement means M_B 20 is not necessarily comprised in the ventilator system 10 according to the present invention. Rather, the system 10 is adapted for receiving second data D2 from such an entity or device as schematically indicated by the connecting arrow. It is however contemplated that a blood measurement means M_B could be comprised in the system 10 and integrated therein. In this embodiment, the mechanical ventilator system comprises at least the ventilator means VENT 11, the measurement means M_G (1 and 2) 11 (*a* and *b*), and the control means CON 12. The physiological model MOD is implemented on the control means, e.g. in an appropriate computing entity or device.

In one variant of the invention, the third data D3 could be estimated or guessed values being indicative of the respiratory feedback in the blood of said patient, preferably based on the medical history and/or present condition of the said patient. Thus, values from previously (earlier same day or previous days) could form the basis of such estimated guess for third data D3.

The control means is adapted for using both the first data D1 indicative of parameters of the inspired gas, the second data D2 indicative of changes of respiratory feedback in expired air 6*b*, and the third data D3 indicative of the respiratory feedback in the blood 7. By the use of preference functions the system translates D1, D2 and D3 into scoring values displayed in a coordinate system 14 in a graphical user interface (GUI) 13.

Figure 2:
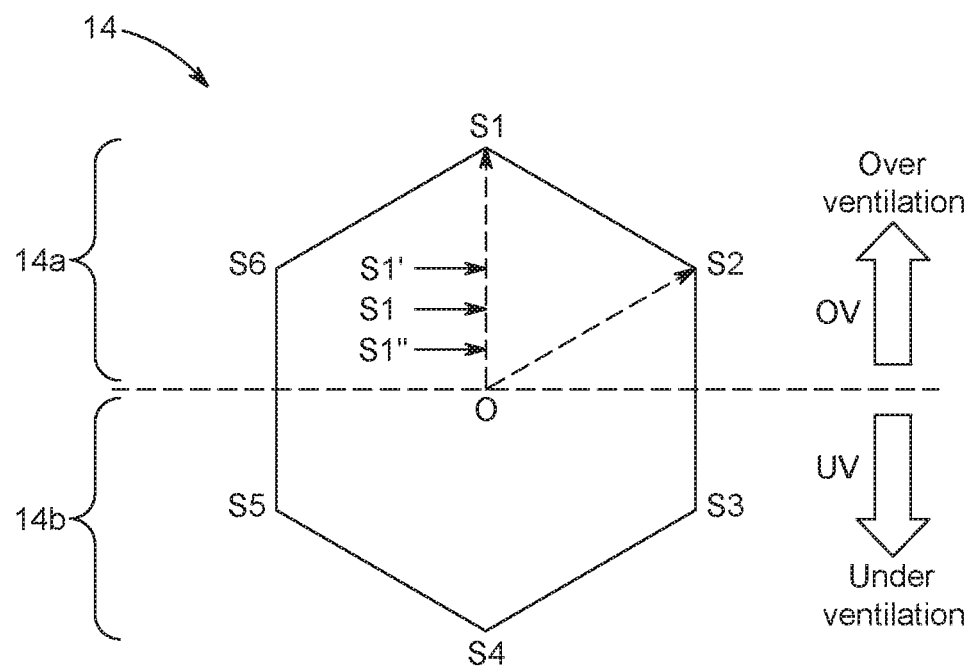
FIG. 2 shows a preferred output format in the GUI in a schematic format.
Figure 2:
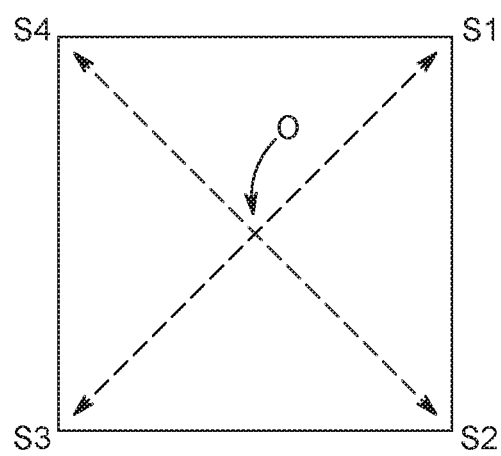
Figure 2:
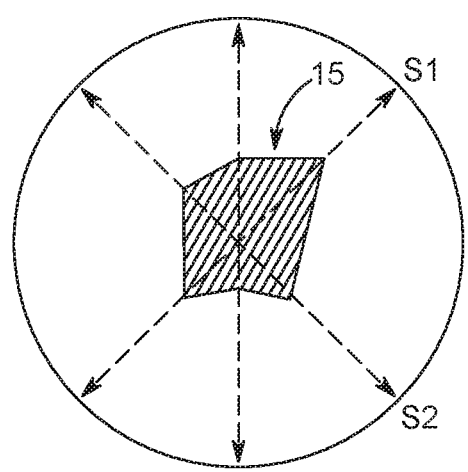
Figure 3:
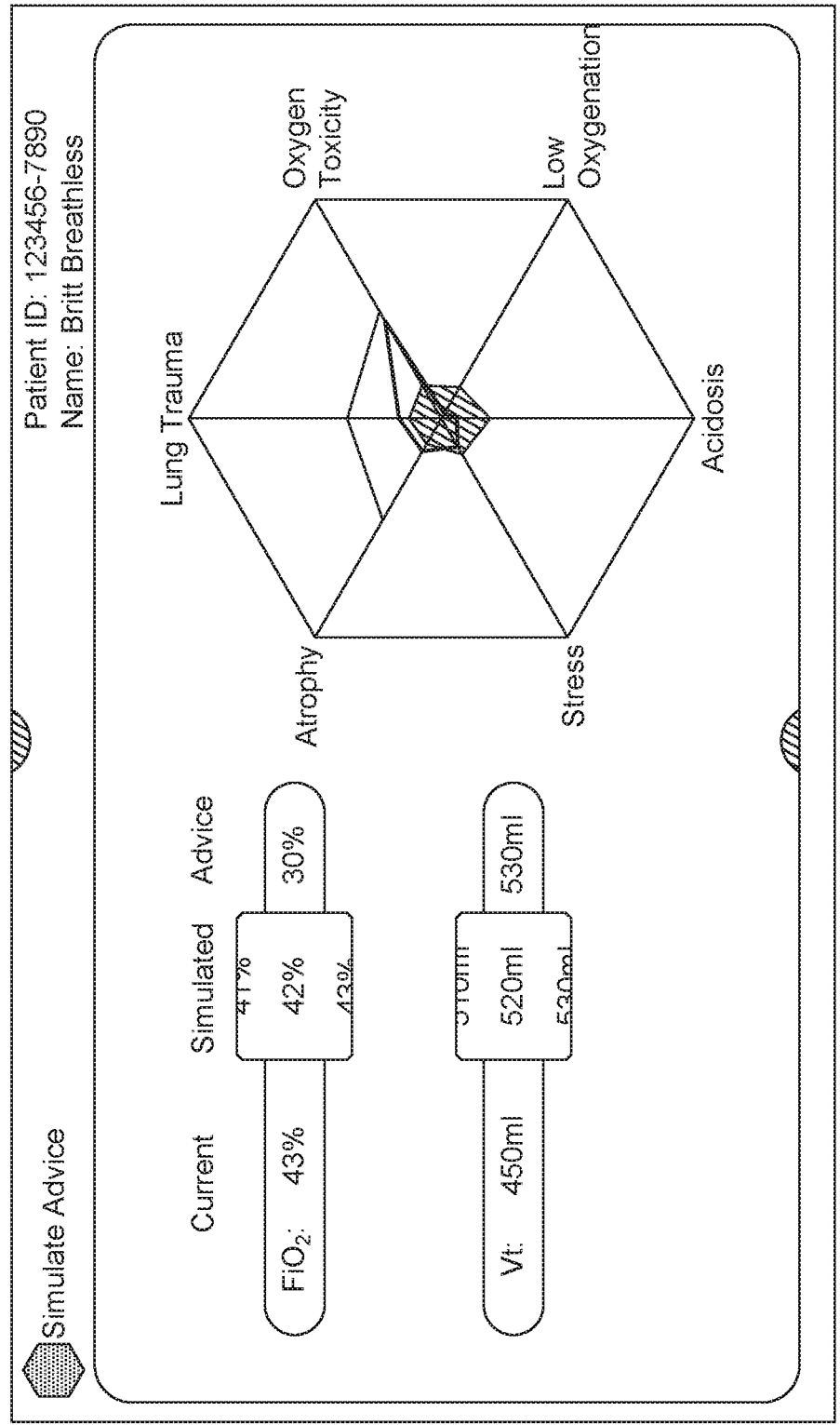
FIG. 3 shows a screenshot of a preferred output format in the GUI.

The principle of this invention is further exemplified in FIGS. 2 and 3.

FIG. 2A illustrates an example of a multidimensional coordinate system 14, in here displayed as a hexagon, with the scoring values S1-S6 being displayed at an axis from the center, or origin, O towards each corner of the hexagon. The scoring values being displayed in the upper half 14*a* is indicative of over-ventilation of the patient, whereas the scoring values being displayed in the lower half 14*b* is indicative of under-ventilation.

It is to be understood that scoring values representative for current status S1, modelled/simulated status S1' (based on user input) and advice S1" based on a physiological model implemented in the system may all be displayed. The three different values may be displayed simultaneously or by selection of the user. The same can be the case for other scoring values.

FIG. 2B shows an example of a coordinate system shaped as a square. Such square will then only display two scoring pairs, S1 vs. S4, and S2 vs. S3, respectively. FIG. 2C shows a circular coordinate system, where the scoring values are displayed on an axis going from the center towards a point on the circumference of the circle. In FIG. 2C, an area 15 constituted by the displayed scoring values is also displayed. Such an area may be indicative of the overall quality of the ventilator settings. Again such areas may be displayed for current status, modelled/simulated status (based on user input) and advice based on a physiological model implemented in the system. Thus, the system apply the physiological model (MOD) to generate said advice basing its advice on a model which minimizes the area of the polygon zones, without any of the scoring values exceeds predetermined threshold levels. Thus, the system may try to minimize the scoring values and thus also minimize the area/preference zone in the coordinate system.

FIG. 3 is an actual screenshot of how data may be presented on a monitor, with actual scoring values presented. Areas 15 are also presented. To the right, the multi-dimensional coordinate system 14 is shown, i.e. a hexagon, the upwards direction in the figure being the direction representing over-ventilation OV and the downwards representing under-ventilation UV as in FIG. 2. To the left in FIG. 3, the current values, and simulated values of the respiratory volume in a single breath Vt and the fraction of inhaled oxygen $FiO_2$, respectively, are shown. Additionally, the 'Advice' according to the present is displayed next to the simulated values.

Figure 4:
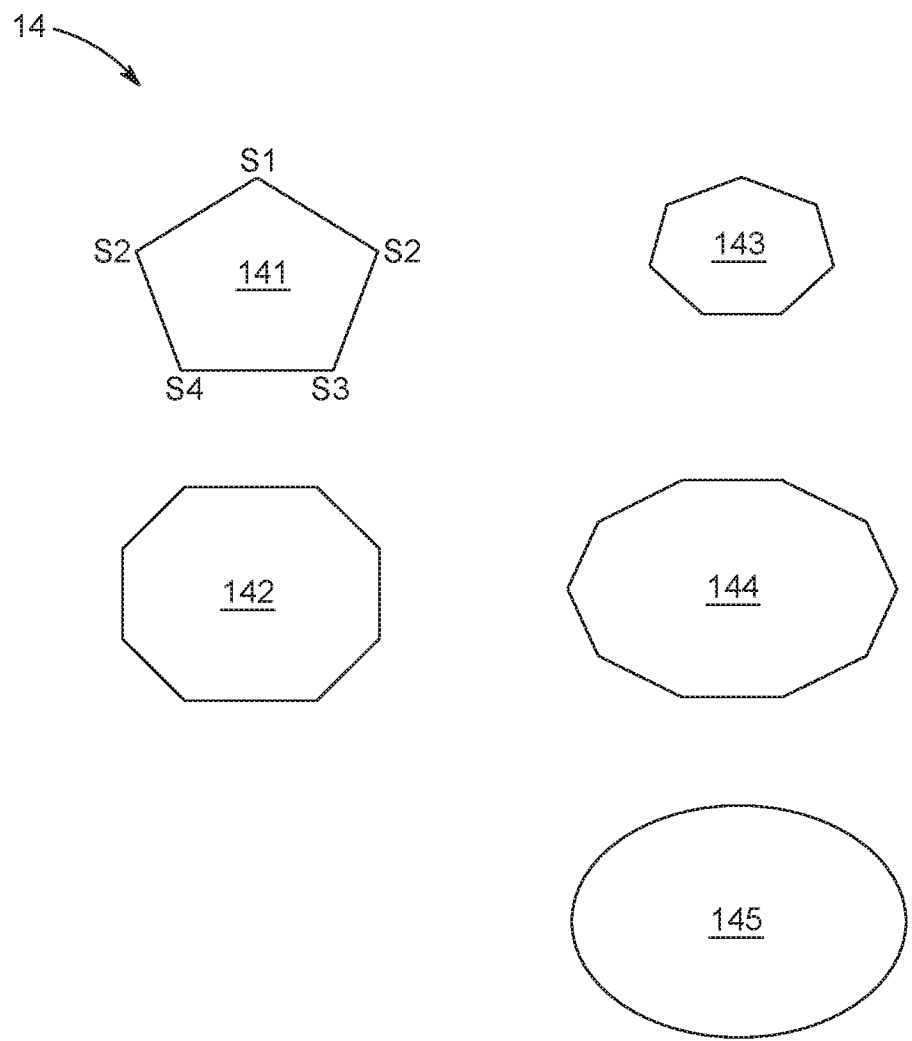
FIG. 4 shows examples of output formats in the GUI.

FIG. 4 shows other shapes (pentagon 141, octagon 142, heptagon 143, decagon 144, non-polygon 145) which may be implemented in a system according to the invention. The number of corners in the polygon may depend on the number of scoring pairs included in the system. Notice that for a polygons with an uneven number of corners, e.g. a pentagon, there will be one or more pairs of scorings values displayed, but at least one scoring value will be unpaired. Thus, in the pentagon shown one scoring value, e.g. S5, may be unpaired.

Figure 5:
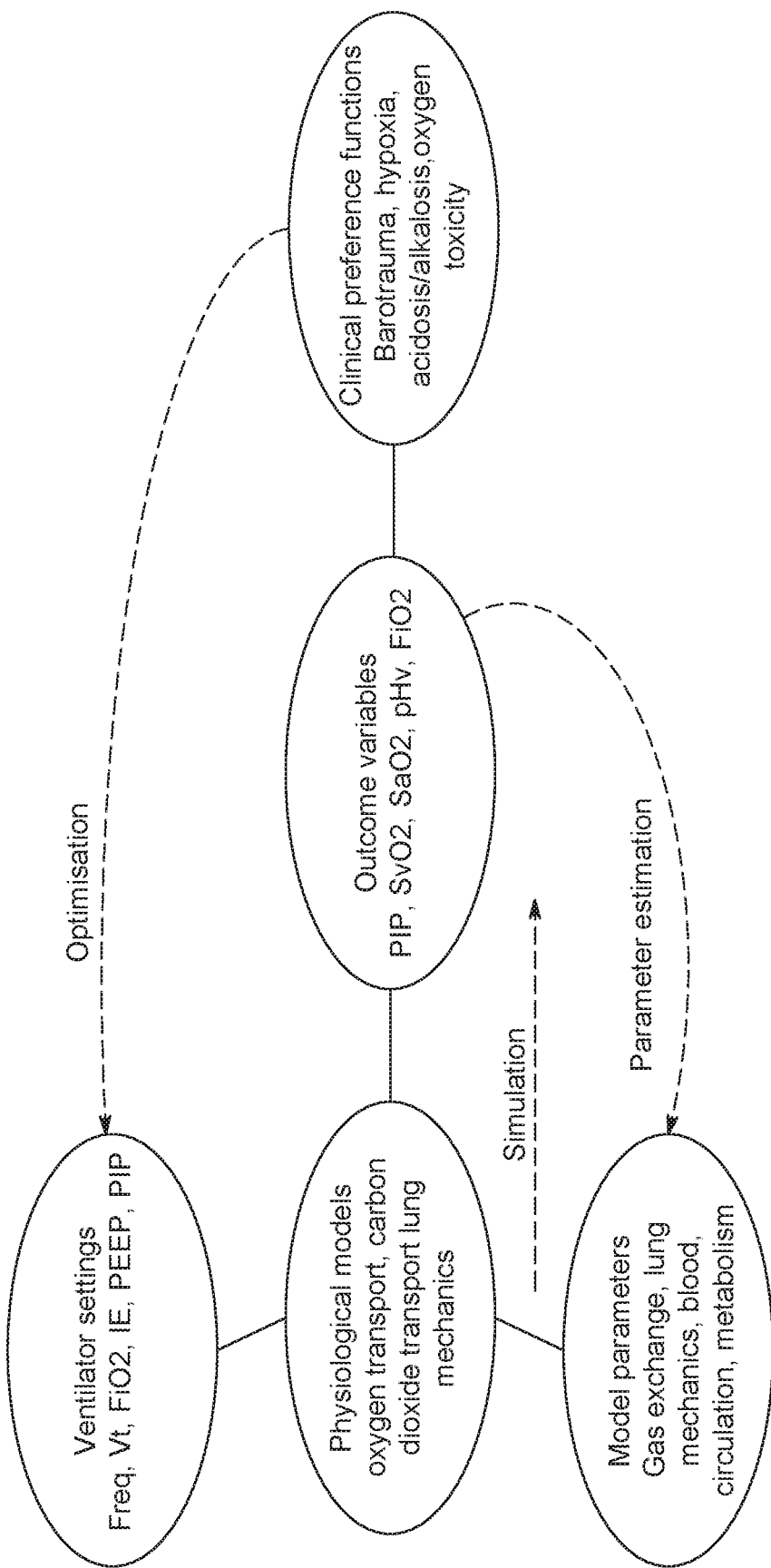
FIG. 5 shows the structure of a decision support system according to the invention, illustrating the components of the system (ovals) and the functionality (dashed lines).

FIG. 5 illustrates the conceptual model behind the system according to the invention. The core of the system is a set of physiological models describing pulmonary gas exchange, acid-base chemistry, lung mechanics etc. the system tunes these models to the individual patient such that they describe accurately current measurements, labelled "Outcome Variables" in the figure.

The ovals illustrates components of the system, which includes
- ventilator settings (f, Vt, FiO2, LE-ratio, PEEP and PIP);
- model parameters (shunt, fA2, Vd, compliance, DPG, Hb, COHb, MetHb, temp, Q, VO2 and VCO2);
- physiological models and their variables (FetCO2, FetO2, SaO2, PaO2, PaCO2, pHa, SvO2, PvO2, PvCO2, and pHv);
- those variables selected as surrogate outcomes (PIP, SvO2, SaO2, pHv and FiO2); and
- functions describing clinical preference (barotrauma, hypoxia, acidosis-alkalosis, oxygen toxicity).

Figure 6:
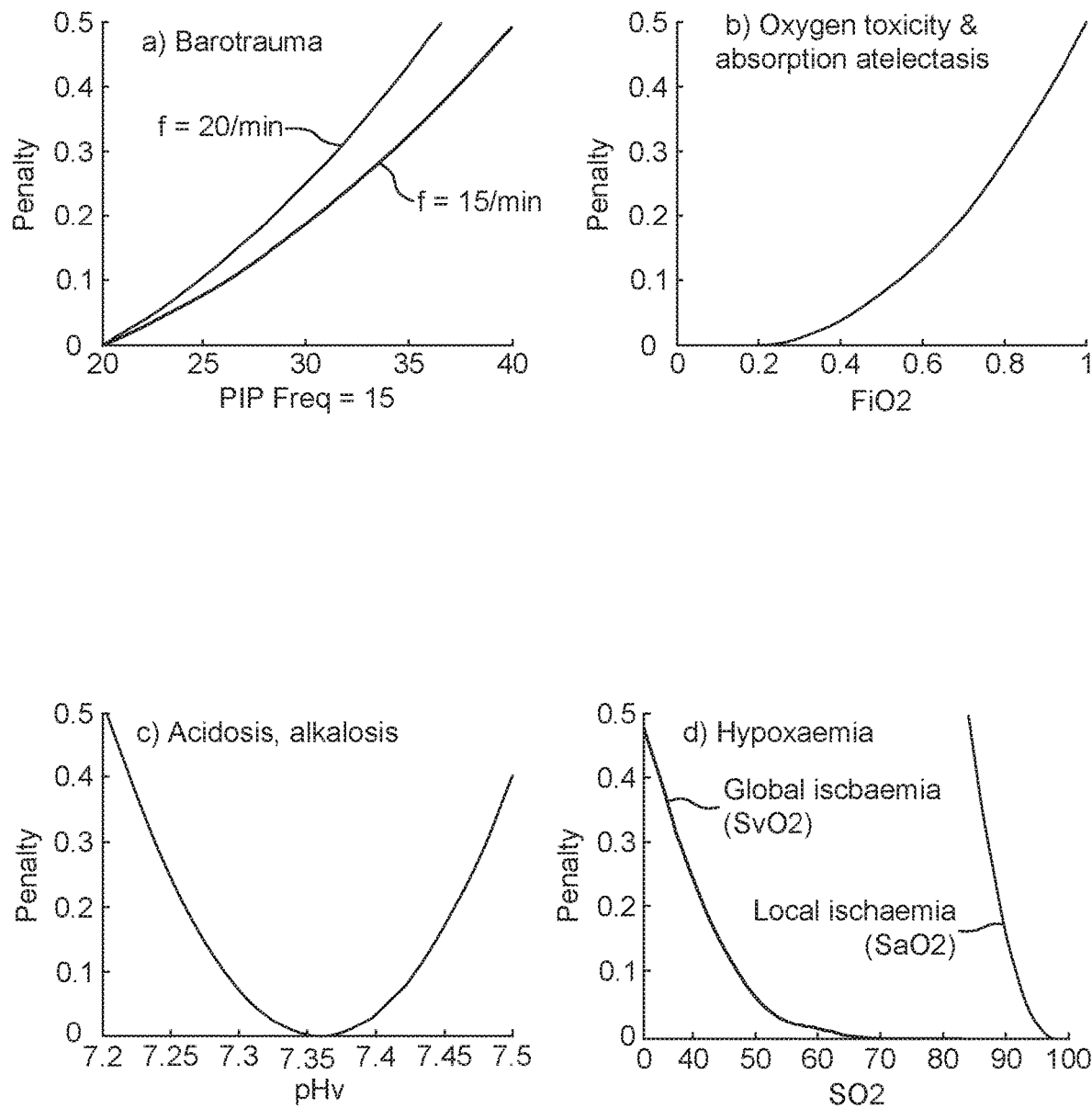
FIG. 6 shows examples of preference functions (CPF) where physiological variables and ventilator settings are translated into a unified scale (scoring values).

Once tuned, the models are used by the system to simulate the effects of changing ventilator settings. These simulations are then used with a set of "Clinical preference functions" (CPF). Some of these functions are illustrated in FIG. 6 and describe clinical opinion as to the outcome variables. For example, an increased inspiratory volume will reduce an acidosis of the blood while detrimentally increasing lung pressure. Appropriate ventilator settings Vt_SET therefore imply a balance between the preferred value of pH weighted against the preferred value of lung pressure. A number of these balances exist, and the clinical preference functions quantitatively weight these, calculating a total score for the patient for any possible ventilation strategy. As the individual preference scores all range between 0 and 0.5 and the patients total score is a sum of these, then the patients score can range between 0 and 2, with 0 being the best condition and 2 the worst condition. The model simulations and preference functions are then used together in a process called "optimization" where the ventilator settings resulting in simulations giving the preferred patient score, i.e. the lowest, are found. These are then said to be the optimal ventilator settings and are a target advice. If the target advice is a substantial distance from current ventilator settings then "advice steps" may be generated, these steps represent a clinically reasonable step toward the target advice without overly aggressive modifications in ventilator settings.

Figure 7:
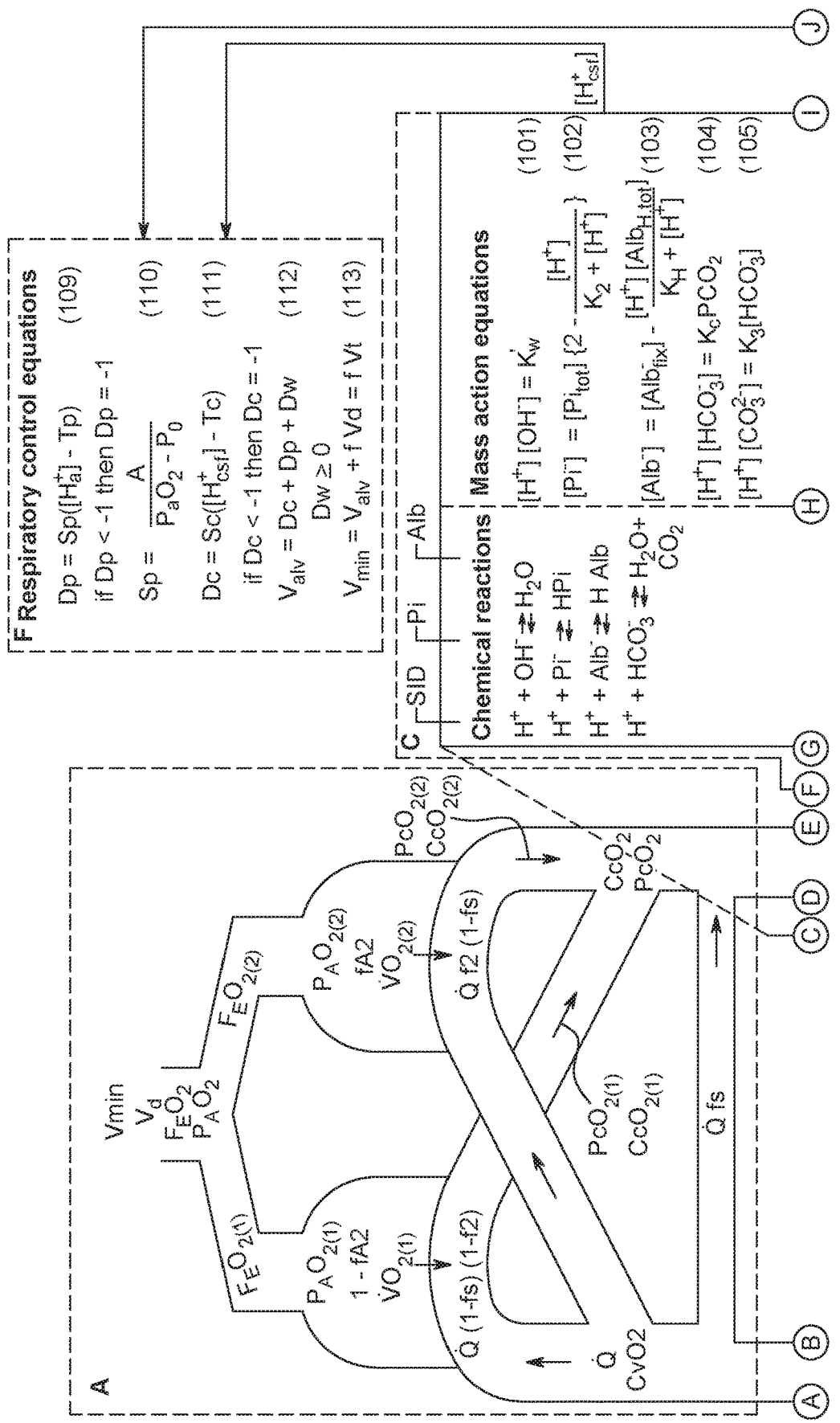
FIG. 7 illustrates a set of mathematical model components of a decision support system (DSS) including the mathematical representation of a physiological model of respiratory control.
Figure 7:
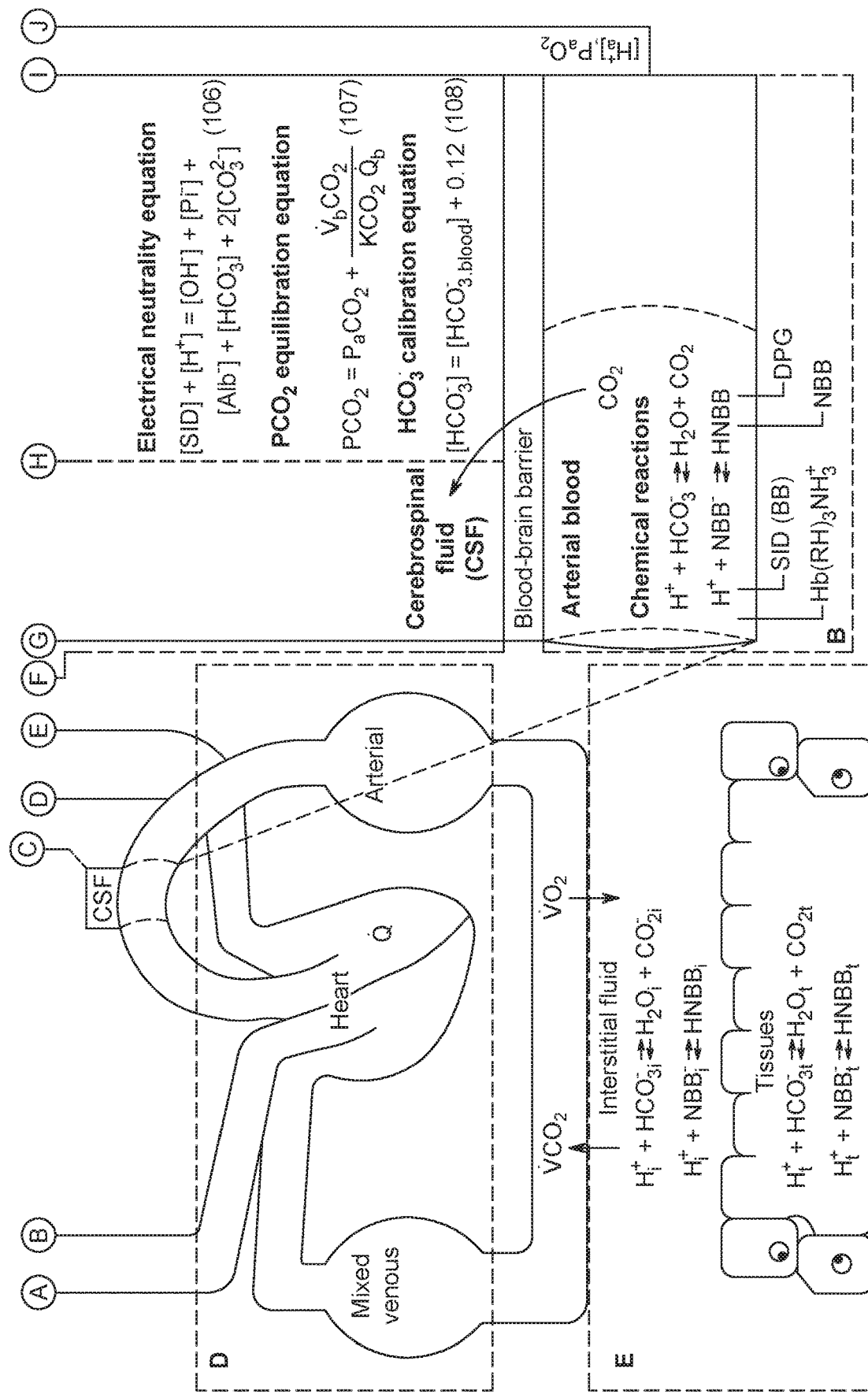

FIG. 7 illustrates the set of mathematical model components of a decision support system (DSS) including the mathematical representation in the form of physiological model of respiratory control that may be applied in the context of the present invention.

The DSS includes models of: pulmonary gas exchange (A); acid-base status and oxygenation of blood (B); acid-base status of CSF (C); cardiac output, and arterial and mixed venous pools (D); interstitial fluid and tissue buffering, and metabolism (E); and chemoreflex model of respiratory control (F).

FIG. 7A illustrates the structure of the model of ventilation and pulmonary gas exchange. FIG. 7B illustrates the structure of the model of oxygenation and acid-base status in the blood. FIG. 7C illustrates Duffin's model of CSF with appropriate model constants [3, 4]. This model includes mass-action equations describing water, phosphate and albumin dissociation plus the formation of bicarbonate and carbonate, and an equation representing electrical neutrality (equations 101-106). In addition, equation (107) is used to describe the equilibration of PCO$_2$ with arterial blood across the blood-brain barrier. Equation (108) is a modification to Duffin's model which allows calibration of the CSF to conditions where blood bicarbonate, and hence buffer base (BB) or strong ion difference (SID) are modified, such as metabolic acidosis where blood bicarbonate is reduced, or chronic lung disease where blood bicarbonate is increased.

The model illustrated in FIG. 7 includes compartments representing CO$_2$ transport and storage including the arterial and venous compartments, and circulation represented as cardiac output (Q) (FIG. 7D).

FIG. 7E illustrates the model of interstitial fluid and tissue buffering, and metabolism included in the system. This includes oxygen consumption (VO$_2$) and carbon dioxide production (VCO$_2$).

FIG. 7F illustrates the model of respiratory control of Duffin, i.e. equations 109-112. Alveolar ventilation is modeled as a peripheral and central chemoreflex response to arterial and cerebrospinal fluid (CSF) hydrogen ion concentration ([H$^+_a$] and [H$^+_{csf}$]) plus wakefulness drive. Equation (109) describes the peripheral drive (Dp) as a linear function of the difference between [H$^+_a$] and the peripheral threshold (Tp). The slope of this function (Sp) represents the sensitivity of the peripheral chemoreceptors.

Equation (111) describes central drive (Dc) as a linear function of the difference between [H$^+_{csf}$] and the central threshold (Tc). The slope of this function (Sc) represents the sensitivity of central chemoreceptors. Equation (112) describes the alveolar ventilation as the sum of the two chemoreflex drives and the wakefulness drive (Dw). Equation (113) describes the minute ventilation as alveolar ventilation plus ventilation of the dead space, that is equal to the product of tidal volume (Vt) and respiratory frequency (f).

The model described above can be used to simulate respiratory control. The model enables simulation of the control of alveolar ventilation taking into account pulmonary gas exchange, blood and CSF acid-base status, circulation, tissue and interstitial buffering, and metabolism.

Figure 8:
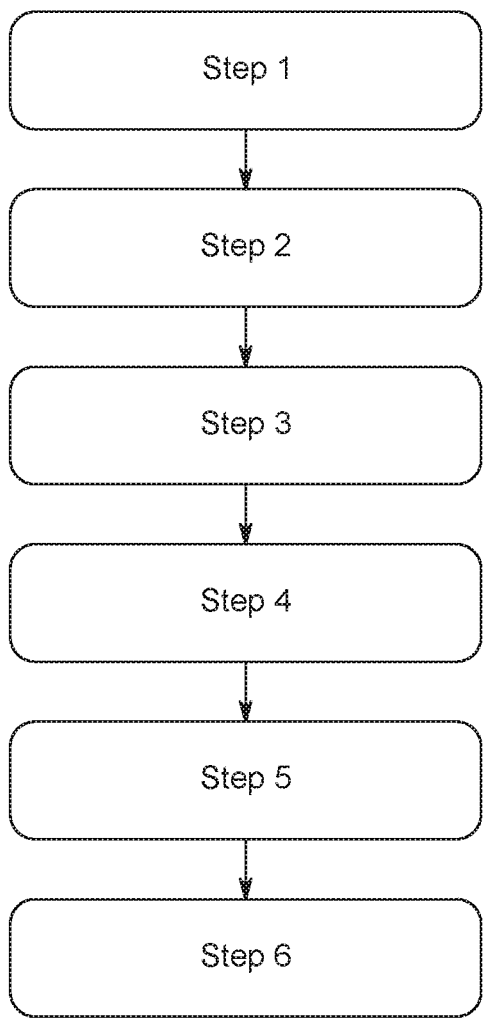
FIG. 8 is a schematic flow chart of a method according to the invention.

FIG. 8 is a schematic flow chart of a method according to the invention. The invention thus relates to a method for operating a mechanical ventilation system for respiration aid of an associated patient 5, P, the system being adapted for providing decision support for choosing a ventilation strategy of said patient, the method comprising:

Step 1 providing ventilator means 11, VENT capable of mechanical ventilating said patient with air and/or one or more medical gases;

Step 2 providing control means 12, CON, the ventilator means being controllable by said control means by operational connection thereto Vt_SET;

Step 3 providing first measurement means 11a, M_G1 arranged for measuring parameters of the inspired gas 6a, the first means being capable of delivering first data D1 to said control means; optionally, second measurement means 11b, M_G2 arranged for measuring the respiratory feedback of said patient in expired gas 6b, the second means being capable of delivering second data D2 to said control means;

Step 4 providing third measurement means 20, M_B, arranged for measuring one or more blood values of said patient, the third means being capable of delivering third data D3 to said control means, the control means applying a set of preference functions CPF to convert the first data D1, the third data D3, and optionally the second data D2, of the patient into corresponding scoring values, S1, . . . , S6;

the system comprising a graphical user interface (GUI) 13 with a multi-dimensional coordinate system 14, wherein at least one pair of scoring values is arranged for being displayed in the coordinate system, wherein each pair of scoring values providing Step 5 a first scoring value, S1, S2, and S6, being a translated variable related to over-ventilation of the patient, the first scoring value being displayed at an axis indicative of over-ventilation in a first direction OV in the GUI, the first scoring value being displayed at a distance from a first starting point O corresponding to the first scoring value, and Step 6 a second scoring value, S3, S4, and S5, being a translated variable related to under-ventilation of the patient, the second scoring value being displayed at an axis being indicative of under-ventilation in a second direction UV in the GUI, the second scoring value being displayed at a distance from a second starting point O corresponding to the second scoring value.

Figure 9:
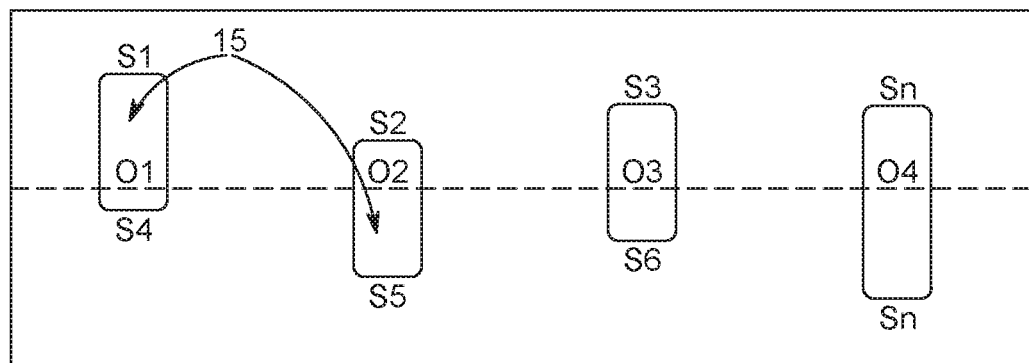
FIG. 9 shows examples of output formats in the GUI with each pair being displayed on a line. The areas of the columns and the areas under the graph represent single preference zones (areas) for each pair. The sum of these individual preference zones represents the overall preference zone for the specific patient.
Figure 9:
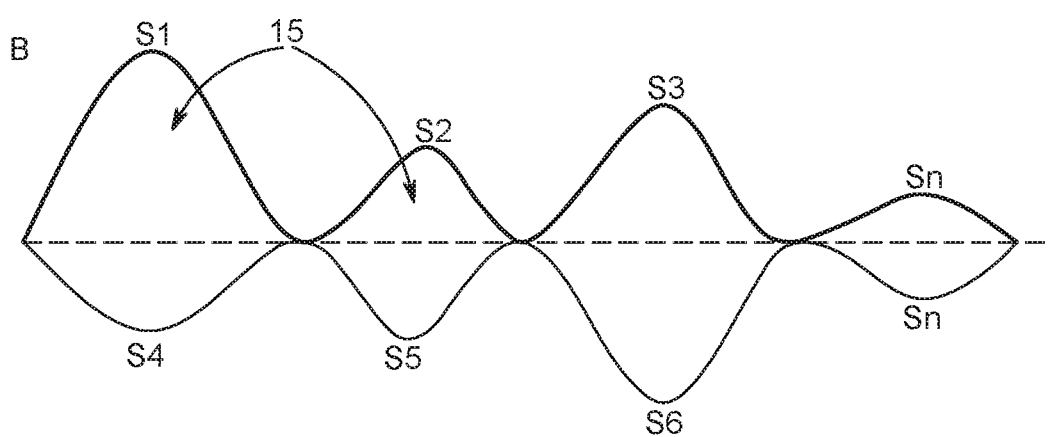
Figure 9:
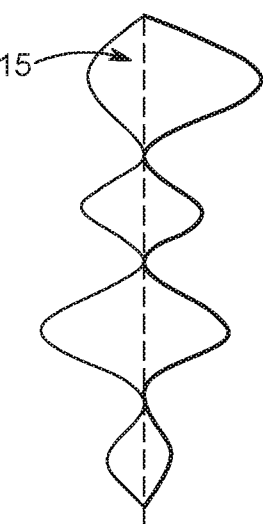
Figure 9:
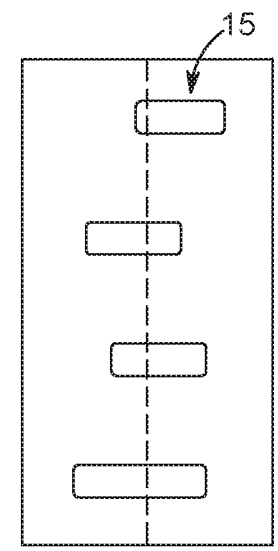

FIG. 9 is illustrations showing alternative ways of displaying the scoring values in the GUI where the values indicative of over-ventilation and under-ventilation are presented on a common horizontal, or vertical axis. Notice that the pairs of scoring values, S1 vs. S4, etc., are then represented at separate centers O1, O2, O3, and O4, in the coordinate system of example A. Similarly, in the coordinate system of examples B, C and D, there are separate centers for the pairs of scoring values. The axis (indicated by the dotted lines in examples A, B, C and D) divides the scoring values into values representative of over- and under-ventilation. It should be noted that embodiments and features described in the context of one of the aspects of the present invention also apply to the other aspects of the invention.

All patent and non-patent references cited in the present application, are hereby incorporated by reference in their entirety.

Glossary

CSF Cerebral spinal fluid
Vt Respiratory volume in a single breath, tidal volume
Vt_SET Respiratory volume settings for mechanical ventilation, tidal volume
$FECO_2$ Fraction of carbon dioxide in expired gas.
$FE'CO_2$ Fraction of carbon dioxide in expired gas at the end of expiration.
$PECO_2$ Partial pressure of carbon dioxide in expired gas.
$PE'CO_2$ Partial pressure of carbon dioxide in expired gas at the end of expiration.
RR respiratory frequency (RR) or, equivalently, duration of breath (including duration of inspiratory or expiratory phase)
pHa Arterial blood pH
PaCO2 Pressure of carbon dioxide level,
SaO2 Oxygen saturation of arterial blood
PpO2 Pressure of oxygen in arterial blood

REFERENCES

1. The Acute Respiratory Distress Syndrome (ARDS) Network (2000) Ventilation with lower tidal volumes as compared with traditional tidal volumes for acute lung injury and the acute respiratory distress syndrome. N. Engl. J Med. 342:1301-1308.
2. Arnstein F. (1997) Catalogue of human error. Br. J. Anaesth. 79:645-656.
3. Wysocki M, Brunner J X. (2007). Closed-Loop Ventilation: An emerging standard of care? Crit. Care Clin. 23:223-240.
4. Arnstein F. (1997) Catalogue of human error. Br. J. Anaesth. 79:645-656.
5. Allerød C, Rees S E, Rasmussen B S, Karbing D S, Kjrgaard S, Thorgaard P, Andreassen S. (2008). A decision support system for suggesting ventilator settings: Retrospective evaluation in cardiac surgery patients ventilated in the ICU. Comput. Meth. Prog. Biomed. 92:205-212.

The invention claimed is:

1. A mechanical ventilation system for respiration aid of an associated patient, the system being adapted for providing decision support for choosing a ventilation strategy of said associated patient, the system comprising:
   a ventilator capable of mechanically ventilating said associated patient with air and/or one or more medical gases;
   a control, the ventilator being controllable by said control by operational connection thereto;
   the control configured to receive a first data indicative of parameters of inspired gas of said associated patient;
   the control further configured to receive a second data indicative of a respiratory feedback of said associated patient in expired gas;
   the control further configured to receive a third data indicative of one or more blood values of said associated patient,
   the control applying a set of preference functions to convert the first data, the third data, and the second data of the associated patient into corresponding scoring values;
   the system comprising a graphical user interface (GUI) with a multi-dimensional coordinate system, wherein multiple pairs of scoring values are arranged for being displayed in the coordinate system, wherein each pair of scoring values comprises a first scoring value and a second scoring value, the first and second scoring values have conflicting effects in response to over-ventilation and under-ventilation in the graphical user interface, wherein:
   the first scoring value is a translated variable related to the over-ventilation of the associated patient, the first scoring value being displayed at a first axis indicative of the over-ventilation in a first direction in the GUI, the first scoring value being displayed at a first distance from a first starting point corresponding to the first scoring value, and
   the second scoring value is a translated variable related to the under-ventilation of the associated patient, the second scoring value being displayed at a second axis indicative of the under-ventilation in a second direction in the GUI, the second scoring value being displayed at a second distance from a second starting point corresponding to the second scoring value,
   wherein the first scoring value and the second scoring value in each pair of scoring values represent opposite clinical preferences, and different pairs of scoring values represent clinical preferences associated with different physiological variables.

2. The system according to claim 1, wherein each pair of plotted scoring values have a common starting point in the multi-dimensional coordinate system, wherein the first starting point and the second starting point are the common starting point.

3. The system according to claim 1, wherein the first and second scoring values displayed closer to the first and second starting points, respectively, are indicative of lower associated patient risk than values plotted at greater distance from the first and second starting points, respectively.

4. The system according to claim 1, wherein the first and second scoring values of each pair are displayed in opposite directions.

5. The system according to claim 1, wherein the multi-dimensional coordinate system has an outer shape being a polygon, each corner in the polygon and the center of the polygon representing a scoring axis of the scoring values, along which scoring axis the scoring values are plotted.

6. The system according to claim 5, wherein the polygon has an even number of corners.

7. The system according to claim 5, wherein the GUI presents a value and/or indicator for an area formed by connecting the plotted/displayed first and second scoring values connected with lines forming the polygon.

8. The system according to claim 1, wherein the multi-dimensional coordinate system is a circle or circular shape, and wherein the first and second scoring values are plotted or displayed along a circle axis between a circumference of the circle or circular shape and a center of the circle or circular shape.

9. The system according to claim 1, wherein the first and second starting points for each pair begin at different points at a line in the multi-dimensional coordinate system dividing the coordinate system into two halves, one half indicative of the over-ventilation of the associated patient and the second half indicative of the under-ventilation of the associated patient.

10. The system according to claim 1, wherein the first and second scoring values represent patient risk values wherein all the patient risk values have been normalized to have comparable patient risk values.

11. The system according to claim 1, wherein the coordinate system is divided by a line through the center, dividing the coordinate system into two halves, one half indicative of the over-ventilation of the associated patient and the second half indicative of the under-ventilation of the associated patient.

12. The system according to claim 1, wherein the neighbouring displayed scoring values are connected with lines or curves forming an area in the GUI.

13. The system according to claim 1, wherein the system is arranged for presenting an overview over the first and second scoring values and/or areas determined at earlier time points.

14. The system according to claim 1, wherein decreasing areas over time is indicative of improved ventilation parameters and wherein increasing areas over time is indicative of suboptimal ventilation parameters.

15. The system according to claim 1, wherein the system is arranged to output the first and second scoring values and/or areas in the GUI based on suggested input ventilation parameters by a user.

16. The system according to claim 1, wherein the system is arranged to output an advice for a ventilation strategy of the associated patient and display modelled additional scoring values and/or areas based on said advice, the system using a physiological model to generate said advice.

17. The system according to claim 1, wherein the first and second scoring values have the conflicting effects with respect to:
  mechanical lung trauma vs. acidosis;
  oxygen toxicity vs. low oxygenation;
  stress vs. ventilator dependency;
  Volutrauma vs. atelectrauma and/or
  Alveolar derecruitment vs. adverse heamodynamic effects of high ventilator pressure.

18. The system according to claim 1, wherein the first and second scoring values have the conflicting effects with respect to:
  mechanical lung trauma vs. acidosis;
  oxygen toxicity vs. low oxygenation; and/or
  stress vs. ventilator dependency.

19. The system according to claim 1, wherein the system is arranged for receiving one or more therapeutic input parameters relating to the associated patient, wherein the system is arranged to recalibrate the preference functions based on said therapeutic input parameters, thereby recalibrating the scoring values generated by the system.

20. The system according to claim 19, wherein the system is adapted for changing the weight of each preference function based on the therapeutic input parameters.

21. The system according to claim 19, wherein the therapeutic input parameters are selected from a group consisting of information on head trauma, age, sex, clinical history, medication, and/or associated patient group.

22. The system according to claim 1, wherein a colouring of lines and/or areas are indicative of a total patient risk.

23. The system according to claim 1, wherein a colouring of lines and/or areas are indicative of extra patient risk in addition to risks presented on the axes.

24. A computer system for cooperating with and/or controlling an associated mechanical ventilation system for respiration aid of an associated patient, the associated mechanical ventilation system being of the type having:
  a ventilator capable of mechanically ventilating said associated patient with air and/or one or more medical gases;
  a first control, the ventilator being connectable to said first control by operational connection thereto;
  the first control configured to receive a first data indicative of parameters of inspired gas of said associated patient;
  the first control further configured to receive a second data indicative of a respiratory feedback of said associated patient in expired gas;
  the first control further configured to receive a third data indicative of one or more blood values of said associated patient, the computer system being adapted for providing decision support for choosing a ventilation strategy of said associated patient,
the computer system comprising:
  a second control applying a set of preference functions to convert the first data, the third data, and the second data of the associated patient into corresponding scoring values; and
  a graphical user interface (GUI) with a multi-dimensional coordinate system, wherein multiple pairs of scoring values are arranged for being displayed in the coordinate system, wherein each pair of scoring values comprises a first scoring value and a second scoring value, the first and second scoring values have conflicting effects in response to over-ventilation and under-ventilation in the graphical user interface, wherein:
  the first scoring value is a translated variable related to the over-ventilation of the associated patient, the first scoring value being displayed at a first axis indicative of the over-ventilation in a first direction in the GUI, the first scoring value being displayed at a first distance from a first starting point corresponding to the first scoring value, and
  the second scoring value is a translated variable related to the under-ventilation of the associated patient, the second scoring value being displayed at a second axis indicative of the under-ventilation in a second direction in the GUI, the second scoring value being displayed at a second distance from a second starting point corresponding to the second scoring value, wherein the first scoring value and the second scoring value in each pair of scoring values represent opposite clinical preferences, and different pairs of scoring values represent clinical preferences associated with different physiological variables.

25. A non-transitory storage medium comprising a computer program product having instructions embodied thereon, the computer program product, when executed by a computing device or system, causes the computing device or system to:

apply a set of preference functions to convert a first data indicative of parameters of inspired gas of a ventilated patient; a second data indicative of a respiratory feedback of the ventilated patient in expired gas; and a third data indicative of one or more blood values of the ventilated patient, into corresponding scoring values, display multiple pairs of scoring values in a multi-dimensional coordinate system, wherein each pair of scoring values comprises a first scoring value and a second scoring value, the first and second scoring values have conflicting effects in response to over-ventilation and under-ventilation in a graphical user interface, wherein:

the first scoring value is a translated variable related to the over-ventilation of the ventilated patient, the first scoring value being displayed at a first axis indicative of the over-ventilation in a first direction in the multi-dimensional coordinate system, the first scoring value being displayed at a first distance from a first starting point corresponding to the first scoring value, and the second scoring value is a translated variable related to the under-ventilation of the ventilated patient, the second scoring value being displayed at a second axis indicative of the under-ventilation in a second direction in the multi-dimensional coordinate system, the second scoring value being displayed at a second distance from a second starting point corresponding to the second scoring value, wherein the first scoring value and the second scoring value in each pair of scoring values represent opposite clinical preferences, and different pairs of scoring values represent clinical preferences associated with different physiological variables.

* * * * *